United States Patent
Kubicek et al.

(10) Patent No.: US 10,919,823 B2
(45) Date of Patent: Feb. 16, 2021

(54) CHLORINOLYSIS PROCESS FOR PRODUCING CARBON TETRACHLORIDE

(71) Applicant: SPOLEK PRO CHEMICKOU A HUTNI VYROBU A.S., Usti nad Labem (CZ)

(72) Inventors: Pavel Kubicek, Decin (CZ); Vlastimil Briza, Usti nad Labem (CZ); Tomas Pittner, Chlumec (CZ); Tomas Riedel, Usti nad Labem (CZ)

(73) Assignee: SPOLEK PRO CHEMICKOU A HUTNI VYROBU A.S., Usti Nad Labem (CZ)

( * ) Notice: Subject to any disclaimer, the term of this patent is extended or adjusted under 35 U.S.C. 154(b) by 0 days.

(21) Appl. No.: 16/334,015

(22) PCT Filed: Aug. 29, 2017

(86) PCT No.: PCT/CZ2017/000054
§ 371 (c)(1),
(2) Date: Mar. 17, 2019

(87) PCT Pub. No.: WO2018/041278
PCT Pub. Date: Mar. 8, 2018

(65) Prior Publication Data
US 2019/0292118 A1    Sep. 26, 2019

(30) Foreign Application Priority Data
Sep. 2, 2016 (CZ) ................. CZ2016-532

(51) Int. Cl.
*C07C 17/10* (2006.01)
*B01D 3/14* (2006.01)
*C07C 17/383* (2006.01)
*C07C 17/395* (2006.01)
*C07C 17/38* (2006.01)
*C07C 17/06* (2006.01)

(52) U.S. Cl.
CPC .............. *C07C 17/10* (2013.01); *B01D 3/143* (2013.01); *C07C 17/06* (2013.01); *C07C 17/38* (2013.01); *C07C 17/383* (2013.01); *C07C 17/395* (2013.01)

(58) Field of Classification Search
CPC ........ C07C 17/00; C07C 17/10; C07C 17/269; C07C 17/361; C07C 21/12; C07C 19/041
See application file for complete search history.

(56) References Cited

U.S. PATENT DOCUMENTS

| | | | |
|---|---|---|---|
| 2,440,768 A | | 5/1948 | Churchill |
| 2,442,324 A | * | 5/1948 | Heitz ............... C07C 17/00 570/218 |
| 2,906,681 A | * | 9/1959 | Passler ............. C07C 17/10 204/157.95 |
| 4,661,648 A | | 4/1987 | Franklin |
| 4,689,130 A | | 8/1987 | Masini |
| 5,426,256 A | | 6/1995 | Petrosky |
| 2009/0023963 A1 | | 1/2009 | Wen |
| 2014/0171698 A1 | | 6/2014 | Elsheikh et al. |

FOREIGN PATENT DOCUMENTS

| | | |
|---|---|---|
| EP | 0573920 | 12/1993 |
| EP | 1663920 | 7/2006 |
| GB | 1297392 | 11/1972 |
| WO | WO 2012/098420 | 7/2012 |
| WO | WO 2013/015068 | 1/2013 |
| WO | WO 2013/074324 | 5/2013 |
| WO | WO 2013/096311 | 6/2013 |
| WO | WO 2016/058566 | 4/2016 |
| WO | WO 2016/058567 | 4/2016 |
| WO | WO 2016/058568 | 4/2016 |
| WO | WO 2016/058569 | 4/2016 |
| WO | WO 2017/028826 | 2/2017 |

OTHER PUBLICATIONS

Obrech et al., Carbon tetrachloride and perchloroethylene from chlorine and propane or 1,2-dichloropropane, 1968 (DE 1275040 abstract, Aug. 1968).*
International Search Report dated Dec. 21, 2017 for PCT Application No. PCT/CZ2017/000054.

* cited by examiner

*Primary Examiner* — Jafar F Parsa
(74) *Attorney, Agent, or Firm* — Mark S. Cohen; Pearl Cohen Zedek Latzer Baratz LLP (57) ABSTRACT

A chlorinolysis process for producing carbon tetrachloride comprising providing a chlorination zone at an operating temperature of from 400 to 600° C. with i) chlorine, ii) a C1 chlorinated compound comprising 1 to 3 chlorine atoms and iii) a carbon/second chlorine source to produce a reaction mixture, and, after a residence time, extracting a product mixture from the chlorination zone, the product mixture comprising carbon tetrachloride and optionally perchloroethylene, wherein the product mixture comprises a higher molar content of carbon tetrachloride than perchloroethylene, if present.

28 Claims, 1 Drawing Sheet

CHLORINOLYSIS PROCESS FOR PRODUCING CARBON TETRACHLORIDE

CROSS-REFERENCE TO RELATED APPLICATIONS

This application is a National Phase Application of PCT International Application No. PCT/CZ2017/000054, International Filing Date Aug. 29, 2017, claiming priority of Czech Application No. PV2016-532, filed Sep. 2, 2016, each of which are hereby incorporated by reference.

The present invention relates to processes for producing carbon tetrachloride from a range of carbon-containing feedstocks as well as the compositions obtainable from such processes.

Haloalkanes find utility in a range of applications. For example, halocarbons are used extensively as refrigerants, blowing agents and foaming agents. Throughout the second half of the twentieth century, the use of chlorofluoroalkanes increased exponentially until the 1980's, when concerns were raised about their environmental impact, specifically regarding depletion of the ozone layer.

Subsequently, fluorinated hydrocarbons such as perfluorocarbons and hydrofluorocarbons have been used in place of chlorofluoroalkanes, although more recently, environmental concerns about the use of that class of compounds have been raised and legislation has been enacted in the EU and elsewhere to reduce their use.

New classes of environmentally friendly halocarbons are emerging and have been investigated. Several of these include compounds having low ozone depletion and low global warming potential which have been embraced in a number of applications, especially as refrigerants in the automotive and domestic fields. Examples of such compounds include 2-chloro-3,3,3-trifluoropropene (HCFO-1233xf), 1,3,3,3-tetrafluoropropene (HFO-1234ze), 3,3,3-trifluoropropene (HFO-1243zf), 2,3,3,3-tetrafluoropropene (HFO-1234yf), 1,2,3,3,3-pentafluoropropene (HFO-1225ye), 1-chloro-3,3,3-trifluoropropene (HCFO-1233zd), 3,3,4,4,4-pentafluorobutene (HFO-1345zf), 1,1,1,4,4,4-hexafluorobutene (HFO-1336mzz), 3,3,4,4,5,5,5-heptafluoropentene (HFO-1447fz), 2,4,4,4-tetrafluorobut-1-ene (HFO-1354mfy) and 1,1,1,4,4,5,5,5-octafluoropentene (HFO-1438mzz). For the avoidance of doubt, HFO is used to mean 'hydrofluoroolefin', i.e. an unsaturated compound comprising carbon, hydrogen and fluorine atoms, and HCFO is used to mean 'hydrochlorofluoroolefin', i.e. an unsaturated compound comprising carbon, hydrogen chlorine and fluorine atoms.

While these compounds are, relatively speaking, chemically non-complex, their synthesis on an industrial scale, particularly on a continuous basis, to the required levels of purity is challenging. Many synthetic routes proposed for such compounds use, as starting materials or intermediates, chlorinated alkanes or chlorinated alkenes. Examples of such routes are disclosed in WO2012/098420, WO2013/015068 and US2014/171698.

The conversion of the chlorinated alkane or alkene starting materials to the fluorinated target compounds may be achieved using hydrogen fluoride and optionally transition metal catalysts, for example chromium-based catalysts.

An example of a process for preparing fluoroalkenes is disclosed in WO2013/074324. Further examples of conversions for preparing fluorinated compounds from $C_3$ chlorinated feedstocks include:

1,1,1,2,3-pentachloropropane (HCC-240db) to 2-chloro-3,3,3-trifluoro-1-propene (HCFO-1233xf);
1,1,2,2,3-pentachloropropane (HCC-240aa) to 2-chloro-3,3,3-trifluoro-1-propene (HCFO-1233xf);
1,1,1,2,3-pentachloropropane (HCC-240db) to 2,3,3,3-tetrafluoro-1-propene (HFO-1234yf);
1,1,2,2,3-pentachloropropane (HCC-240aa) to 2,3,3,3-tetrafluoro-1-propene (HFO-1234yf);
1,1,3,3-tetrachloro-1-propene (HCO-1230za) to 1,1,1-trifluoro-3-chloro-2-propene (HCFO-1233zd), 1,1,1,3-tetrafluoro-1-propene (HFO-1234ze), 1,1,1,3,3-pentafluoropropane (HFC-245fa) and mixtures thereof;
1,1,2,3-tetrachloro-1-propene (HCO-1230xa) to 2-chloro-3,3,3-trifluoro-1-propene (HCFO-1233xf);
1,1,2,3-tetrachloro-1-propene (HCO-1230xa) to 2,3,3,3-tetrafluoro-1-propene (HFO-1234yf);
2,3,3,3-tetrachloro-1-propene (HCO-1230xf) to 2-chloro-3,3,3-trifluoro-1-propene (HCFO-1233xf).
2,3,3,3-tetrachloro-1-propene (HCO-1230xf) to 2,3,3,3-tetrafluoro-1-propene (HFO-1234yf);
2-chloro-3,3,3-trifluoro-1-propene (HCFO-1233xf) to 2,3,3,3-tetrafluoro-1-propene (HFO-1234yf);
2,3-dichloro-1,1,1-trifluoropropane (HCFC-243db) to 2-chloro-3,3,3-trifluoro-1-propene (HCFO-1233xf); and
2,3-dichloro-1,1,1-trifluoropropane (HCFC-243db) to 2,3,3,3-tetrafluoro-1-propene (HFO-1234yf).

An example of processes of particular interest are those which start with carbon tetrachloride as the initial feedstock to manufacture two or more chlorinated $C_3$-$C_4$ feedstocks, preferably from a single production line, which can then viably be employed in the preparation of refrigerants or blowing agent components such as 245fa, 1234yf, 1234ze, 1233xf and/or 1233zdE. An example of such a process producing chlorinated feedstocks is disclosed in WO2017/028826. Refrigerant/blowing agent compositions comprising these components at high levels of purity are of commercial value and thus, there is significant interest in processes which can be used to reliably and efficiently produce such highly pure chlorinated compounds on a kilo-ton scale. Of importance to the viability of those processes is the quality of the starting materials, including carbon tetrachloride.

The issue of the formation of impurities during hydrofluorination reactions is of concern. It has been identified that the presence of certain impurities can impede hydrofluorination on an industrial scale (particularly when conducted on a continuous basis), and/or result in the formation of fluorinated compounds which are difficult to separate from the product of interest, which may limit the effectiveness of the product of interest and/or which may have toxicity issues.

The inventors have identified that an effective way to prevent the formation of such impurities (and thus to avoid the need for purification steps which will reduce yield and/or the economic operation of the process) is to employ ultra pure chlorinated feedstocks in the upstream process steps.

It has been further recognised by the inventors that when chlorinated feedstock used in the preparation of fluorinated compounds is itself obtained from a multi-step process, then those upstream steps need to be controlled in order to prevent the cumulative effect of side reactions generating unacceptable impurities.

The purity of chlorinated starting materials will have a significant effect on the success and viability of downstream processes (particularly continuous processes) for preparing fluorinated products. The presence of certain impurities in chlorinated alkane feedstocks may result in side reactions which minimise the yield and/or effectiveness of the target compound. Removal of those impurities through via distillation is also challenging and/or inefficient.

Accordingly, there is a need for high purity chlorinated alkane compounds (as well as efficient processes for preparing such compounds) which may be used in the synthesis of fluorinated compounds mentioned above or other downstream products.

Many multi-step processes for producing halogenated compounds such as 240db, 240fa, 250fb, 1240za, 1230xa, 1230za, of commercial value employ, as a starting material, carbon tetrachloride. Thus the purity and manufacturing efficiency of carbon tetrachloride has a significant impact on the efficiency, feasibility and commercial viability of the overall production of the downstream compounds of interest.

Thus, a demand exists for very high purity carbon tetrachloride as well as for efficient, selective and reliable processes for preparing that compound. Those skilled in the art will recognise that a reduced-step and/or continuous process for obtaining such high quality material will be of particular interest.

Conventionally, the industrial production of carbon tetrachloride is commonly achieved via high-temperature chlorination of $C_{1-3}$ alkanes or chlorinated alkanes, which is known as chlorinolysis or high temperature chlorinating pyrolysis. In such processes, substitution reactions can be conveniently accompanied by rupture of C—C bonds and the products which are obtained are carbon tetrachloride and tetrachloroethene. This is a process which is not fully selective in terms of the products that are obtained and typically results in a mixture of carbon tetrachloride and perchloroethene. Further, the formation of significant amounts of organic impurities (particularly hexa-chlorinated compounds such as hexachlorobenzene, hexachlorobutadiene, hexachloroethane as well as lower-chlorinated benzenes) as well as other low value byproducts, such as HCl, is a well known drawback of the process as conventionally practiced.

Separation of the organic impurities from the products of interest is challenging. Many of the hexa-chlorinated impurities that are formed during chlorinolysis processes are toxic compounds, particularly hexachlorobenzene and hexachlorobutadiene. Thus, chlorinolysis processes are the subject of strict regulations according to the Stockholm Convention on Persistent Organic Pollutants.

Further, the hexa-chlorinated impurities, due to their unusual physical and chemical properties, are difficult to handle and treat using commonly employed separation and disposal techniques. Generally speaking, only expensive proprietary approaches are used to treat waste mixtures comprising those compounds. Thus process modifications which minimise the formation of such compounds are of interest and growing importance in the field.

Examples of disclosures which provide examples of chlorinolysis processes include U.S. Pat. No. 5,426,256. In that document, $C_{1-3}$ optionally chlorinated alkane compounds are subjected to a chlorinolysis process operated at a temperature of 595° C. which results the production of perchloroethylene (as opposed to carbon tetrachloride). While carbon tetrachloride is employed as a reactive diluent, the aim of the process discussed in U.S. Pat. No. 5,426,256 is to produce perchloroethylene over carbon tetrachloride.

EP573920 is a further example of a disclosure of a chlorinolysis process which favours the formation of perchloroethylene over carbon tetrachloride. The reaction temperature reported in the examples of that patent is 609° C., and the exemplified processes resulted in the formation of significant amounts of hexachlorinated impurities, specifically hexachlorobenzene.

GB1297392 exemplifies a chlorinolysis process operated at 590° C. which results in products rich in perchloroethylene or carbon tetrachloride. Those products are then subjected to a treatment step (specifically a condensation step) to facilitate the separation of chlorinated alkane products from hydrogen chloride and chlorine. The specificity of the process towards perchloroethylene or carbon tetrachloride is controlled by including significant amounts of either compound in the reaction mixture; the patent teaches that the use of a mixture rich in carbon tetrachloride will favour the formation of perchloroethylene, and vice versa.

WO2013/096311 presents a chlorination process operated at mild conditions; the examples are worked temperatures in the range of 35° C. to 84° C. The process relies upon the use of a free radical initiator which catalyses the reaction. A higher temperature process also requiring the use of a radical initiator is disclosed in U.S. Pat. No. 4,661,648.

EP1663920 discloses a chlorinolysis process employing, as a starting material, heavy ends obtained from the production of $C_3$+ polychlorinated alkanes by the reaction of carbon tetrachloride and an olefin or chlorinated olefin. In the examples of EP1663920, the process is operated at a temperature of 590° C., and carbon tetrachloride is added to the reaction mixture to perform as a reactive diluent. In example 4, the chlorine feed rate into the reactor was increased in order to favour the production of carbon tetrachloride relative to perchloroethylene.

U.S. Pat. No. 4,661,648 describes a catalysed chlorination, at lower temperatures, of chloroform to produce carbon tetrachloride.

U.S. Pat. No. 4,689,130 describes low temperature catalysed chlorination of chloroform.

Despite these advances in chlorinolysis process technology, there remains a need for a process which can be operated at lower temperatures, which provides a high degree of control over the proportion of carbon tetrachloride:perchloroethylene which is obtained and which minimises the formation of unwanted impurities, particularly the hexa-chlorinated impurities.

Thus, according to a first aspect of the present invention, there is provided a process for producing carbon tetrachloride comprising providing a chlorination zone with i) chlorine, ii) a $C_1$ chlorinated compound comprising 1 to 3 chlorine atoms and iii) a carbon/second chlorine source to produce a reaction mixture, and, after a residence time, extracting a product mixture from the chlorination zone, the product mixture comprising carbon tetrachloride and optionally perchloroethylene, wherein the product mixture comprises a higher molar content of carbon tetrachloride than perchloroethylene, if present.

The processes of the present invention provide the highly efficient production of carbon tetrachloride using a new method of production in which chlorinated $C_1$ compounds are used as feedstock. The process is of sufficient versatility to permit waste products from a range of processes (such as the production of $C_{3-4}$ chlorinated compounds as well as the process of the present invention, including this process itself) to be employed as a carbon/second chlorine source. Advantageously, by recycling these waste products, this ensures efficient re-utilisation of carbon and chlorine therein and the recovery of their value, especially for an overall industrial plant installation which has the integrated full process starting from a carbon tetrachloride feed and continuing downstream to chlorinated $C_3$-$C_4$ feedstocks for e.g. hydrofluorination plant producing the target HFO and/or HCFO(s).

In the process of the invention, the partially chlorinated $C_1$ compound (i.e. one comprising 1, 2 or 3 chlorine atoms) is a component in the reaction mixture. The $C_1$ chlorinated compound comprising 1 to 3 chlorine atoms may comprise chloroform, methyl chloride and/or methylene chloride. The inventors have unexpectedly found that the presence of a partially chlorinated $C_1$ compound minimises the formation of unwanted impurities, particularly hexa-chlorinated organic impurities, and favours the formation of carbon tetrachloride over perchloroethylene.

Significantly, the use of the $C_1$ chlorinated compound in the feedstock increases the production capacity for carbon tetrachloride. This is illustrated in the examples which demonstrate that if a $C_1$ chlorinated compound (in that case, chloroform) is present in the reaction mixture, the CTC capacity can be increased substantially without any change in the reactor or chlorine recycling system.

The inventors have found that the proportion of the partially chlorinated $C_1$ compound in the total feeds into the chlorination zone affects the molar ratio of carbon tetrachloride and perchloroethylene obtained in the product mixture. Thus, in embodiments of the invention, the partially chlorinated $C_1$ compound makes up at least about 50%, at least about 60%, at least about 70%, at least about 80%, or at least about 90% by weight of the total feed into the chlorination zone.

The usage of the partially chlorinated $C_1$ compound as a component in the reaction mixture has been found to usefully increase a mean residence time of the reactor, for example from a few seconds to 15 to 20 seconds which provides greater thermodynamic control over the chlorination reaction. As a comparison, if a comparative process is operated using methane instead of chloroform, with no other changes made to the reaction conditions or apparatus, the mean residence time in the same reactor will be significantly reduced, e.g. by a factor of 3 to 4 times. This is due to the formation of extremely large quantities of HCl by-product and the evolution of significant heat of reaction, in the methane case, which has to be compensated through the use of substantial amounts of diluent/s. Further, additional diluents have to be fed into the chlorination zone in order to keep the reaction mixture (which contains chlorine and methane) out of potentially explosive range.

The $C_1$ chlorinated compound comprising 1 to 3 chlorine atoms may have a purity of at least about 95%, about 97%, about 98%, about 99%, about 99.5%, about 99.7%, about 99.8% or about 99.9% by weight. Additionally or alternatively, the $C_1$ chlorinated compound comprising 1 to 3 chlorine atoms may have a moisture content of about 200 ppm or less, about 100 ppm or less, about 50 ppm or less or about 25 ppm or less. Further, the $C_1$ chlorinated compound comprising 1 to 3 chlorine atoms may have an oxygen content of about 200 ppm or less, about 100 ppm or less, about 50 ppm or less or about 25 ppm or less.

Additionally, bromochloromethane and other bromine-containing $C_1$ compounds can be converted to chlorobromo $C_1$ compounds (e.g. bromodichloromethane and bromotrichloromethane) in processes of the present invention. This may be problematic as, owing to similar boiling points, such compounds are difficult to separate from the carbon tetrachloride product of interest. Accordingly, where possible, the content of bromine-containing $C_1$ compounds in the $C_1$ chlorinated alkane compound comprising 1 to 3 chlorine atoms may be less than about 2000 ppm, less than about 1000 ppm, less than about 500 ppm, less than about 200 ppm, about 100 ppm or less, about 50 ppm or less or about 25 ppm or less.

In embodiments of the invention, the $C_1$ chlorinated compound comprising 1 to 3 chlorine atoms may comprise a stabiliser. Examples of stabilisers that may be employed include compounds optionally substituted pentene, for example amylene.

A further advantage of the present invention is that the process can be viably employed to produce carbon tetrachloride from a wide range of carbon/second chlorine source materials. The purity requirements on the carbon/second chlorine source are relatively modest as compared to certain prior art chlorinolysis processes which require the use of purified optionally chlorinated alkane or alkene starting materials. The present invention therefore additionally permits the recovery of carbon and chlorine value back to carbon tetrachloride.

In embodiments of the invention, the number of carbon atoms in the carbon tetrachloride and perchloroethylene net produced in the chlorination zone is more than about 95%, more than about 96%, more than about 97%, more than about 98% or more than about 99% of the number of carbon atoms in the starting materials. For clarity, the term 'net produced' means that any internal recycles of the reactor system or diluents containing products are considered as internal streams (within the battery limits) and are not calculated in such a ratio (see FIG. 1) and therefore the net production flow is calculated based on Line 15 mass flow and composition and/or based on outlet pure product stream flows from distillation unit, which is not visible on such schematic FIG. 1. If any external recycles or feed streams introduced via line 3, 4, 37 and/or 50 were applied, then the content of products, if any, in such streams were considered in the net product flow calculations.

Additionally, or alternatively, the molar ratio of HCl produced in the chlorination zone:carbon tetrachloride plus perchloroethylene produced in the chlorination zone is lower than about 2.5:1, lower than about 2:1, lower than about 1.5:1, or lower than about 1.1:1. Advantageously, the process of the present invention results in the reduced formation of HCl as compared to conventional processes which minimise waste.

While the present invention may be operated with the carbon/second chlorine source comprising purified optionally chlorinated alkane or alkene materials (e.g. $C_{1-3}$ chlorinated alkanes or alkenes such as methane, ethane, ethene, propane, propene, dichloroethane and/or dichloropropane having a purity level of at least about 60 weight %, about 80%, about 90%, about 95%, about 97%, about 98%, about 99%, about 99.5%, about 99.7%, about 99.8% or about 99.9%), this is not essential.

This constitutes a major advance over many disclosures in the prior art. The present invention permits the use of a wide range of unpurified materials to be employed as the carbon/second chlorine source.

Examples of carbon/second chlorine sources that may be employed in the process of the present invention, without necessarily being purified, include natural or shale gas and/or partially or totally chlorinated hydrocarbons prepared from natural or shale gas. Impurities that may be present in carbon/second chlorine sources which are, or are derived from, shale gas or natural gas may be of hydrocarbon origin.

In embodiments of the invention, the carbon/second chlorine source may be a chlorinated and/or organic compound-containing byproduct of chemical processes. Examples of processes which result in the formation of byproducts that can be employed as the carbon/second chlorine source in the process of the present invention include the production of carbon tetrachloride (optionally via the process of the present invention) and/or chloroform. On an industrial scale, carbon tetrachloride and chloroform can be produced via various radical chlorination processes (e.g. liquid or gas low temperature photochlorination using UV/VIS light) and/or high temperature gas chlorination of a starting material comprising $C_{1-6}$ hydrocarbons. Other processes use the catalytic oxychlorination of $C_1$ hydrocarbons with HCl and catalytic hydrochlorination of methanol with HCl.

Such a starting material may be a mixture of hydrocarbons, for example at least two compounds which differ in number of carbon atoms. Examples of such a mixture are crude or pre-treated natural gas with a methane content of 75% vol. or higher and/or crude or pre-treated shale gas with a methane content of 75% vol. or higher and/or various side streams from oil and petrochemical processing. In embodiments of the invention, the carbon/second chlorine source may comprise byproducts obtained from the production of carbon tetrachloride and/or chloroform, which byproducts comprise alkanes and/or alkenes and/or chlorinated alkanes and/or chlorinated alkenes, e.g. mono- and multichlorinated methanes, mono- and multichlorinated ethanes and ethenes, mono- and multichlorinated propanes and propenes, mono- and multichlorinated butanes and butenes, and/or mono- and multichlorinated benzenes. In embodiments of the invention, byproducts employed as the carbon/second chlorine source in the process of the present invention which are obtained from the production of carbon tetrachloride and/or chloroform may have a content of $C_1$ compounds of at least about 75%, about 80%, about 85%, about 90% or about 95% by weight.

Further examples of processes which result in the formation of byproducts that can be employed as the carbon/second chlorine source in the process of the present invention include the production of epichlorohydrin, epoxy resin, glycidol, propylene oxide, vinyl chloride, and allyl chloride. Alternatively, processes which result in the formation of byproducts that can be employed as the carbon/second chlorine source in the process of the present invention include the production of chlorinated propanes, chlorinated propenes, chlorinated butanes and chlorinated butenes, e.g. 1,1,1,2,3-pentachloropropane, 1,1,1,3,3-pentachloropropane, 1,1,2,2,3-pentachloropropane, 1,1,1,3-tetrachloropropane, 1,1,2,3-tetrachloropropene, 1,1,3,3-tetrachloropropene, 2,3,3,3-tetrachloropropene and 1,3,3,3-tetrachloropropene, and other chlorinated compounds. Examples of disclosures of processes for producing such compounds can be found in International patent applications nos. WO2016/058566, WO 2016/058567, WO2016/058568, WO2016/058569 and WO2017/028826.

For the avoidance of doubt, the carbon/second chlorine source may be a single waste stream from one of the above-mentioned processes/sources, or may be a combination thereof. Regardless of whether the carbon/second chlorine source is formed from a single waste stream or mixtures of waste streams from such processes, in embodiments of the invention, the carbon/second chlorine source may be stored, e.g. in a tank, prior to use in the process of the present invention. The carbon/second chlorine source may be collected by the waste stream/s being fed into the storage means, optionally from waste stream/s from plants.

Advantageously, the plants in which such processes are operated may be on the same site as the plant in which the process of the present invention is operated.

In embodiments of the invention, the carbon/second chlorine source employed in the process of the present invention may be obtained as a byproduct from one of the above-mentioned processes (or from any other type of process) and/or may comprise $C_{1-6}$ chlorinated hydrocarbons, for example trichloropropenes, tetrachloropropenes, tetrachloropropanes, pentachloropropanes, pentachloropropenes, hexachloropropanes, tetrachloropentanes, pentachloropentanes, cyclic or aliphatic hexachlorohexenes, dichloroethanes, monochlorinated butanes and/or multichlorinated butanes, and/or multi chlorinated butenes.

In embodiments of the present invention in which the carbon/second chlorine source is a byproduct of another process, the byproduct may be a 'lights' byproduct, e.g. comprising $C_{1-3}$ or $C_{1-4}$ chlorinated hydrocarbons optionally having a boiling point below 125° C. Additionally or alternatively, the byproduct may be a 'heavies' byproduct, e.g. comprising $C_{2-6}$, $C_{3-6}$, $C_{2-8}$ or $C_{3-8}$ chlorinated hydrocarbons optionally having a boiling point above 125° C.

In embodiments of the process of the present invention, regardless of the origin of the carbon/second chlorine source, that source may comprise one, two, three, four, five or more optionally chlorinated alkane or alkene compounds.

As will be recognised, the use of byproducts of other processes is highly advantageous as this increases the efficiency and minimises waste and environmental burden of disposing of those byproducts. Further, the use of byproducts of other processes maximises the recovery of value.

In embodiments of the invention, the carbon/second chlorine source may comprise a low quality carbon tetrachloride composition which, for example, has a purity level of less than about 95%, about 90%, about 85% or about 80%, but optionally greater than about 30% or about 50% and/or which comprises hydrocarbon impurities which are difficult to separate from carbon tetrachloride, e.g. which have a boiling point which differs from the boiling point of carbon tetrachloride by about 10° C. or less, or about 5° C. or less.

Examples of hydrocarbon impurities which may be present in low quality carbon tetrachloride and which are challenging to remove include chlorobutane (which has a boiling point 78° C.) and dichloroethane (which has a boiling point of 84° C.) as well as other impurities arising from the degradation of organophosphate ligands, such as those used in the processes disclosed in WO 2016/058566.

As is demonstrated in the accompanying examples, in some embodiments of the invention, crude product mixture formed in the process of the present invention may comprise other compounds, e.g. hexa-chlorinated compounds such as hexachloroethane, hexachlorobutadiene, hexachlorobenzene or trichloroethylene. For downstream applications requiring very low amounts of those compounds, that crude product mixture can be recycled back into the chlorination zone and subjected again to the process of the present invention.

Thus, in an aspect of the present invention, there is provided a process for purifying a low quality carbon tetrachloride composition, the composition comprising carbon tetrachloride and one or more hydrocarbon impurities, comprising providing a chlorination zone with i) chlorine, ii) a $C_1$ chlorinated compound comprising 1 to 3 chlorine atoms and iii) the low quality carbon tetrachloride composition to produce a reaction mixture, and, after a residence time, extracting a product mixture from the chlorination zone, the product mixture comprising carbon tetrachloride and optionally perchloroethylene, wherein the product mixture comprises a higher molar content of carbon tetrachloride than perchloroethylene, if present.

The inventors have identified that the presence of significant levels of phosphorous containing organic compounds in the reaction mixture produced during operation of the process of the present invention may be problematic. Such compounds may be present in the carbon/second chlorine source where that material is a byproduct of another process (eg WO2016/058566) in which an organo phosphate catalyst was employed. Thus, in embodiments of the invention, the phosphorous containing organic compound content in the carbon/second chlorine source which is supplied to the chlorination zone is about 5000 ppm or less, 2000 ppm or less, about 1000 ppm or less, about 500 ppm or less, about 200 ppm or less, about 100 ppm or less, about 50 ppm or less, about 20 ppm or less or about 10 ppm or less.

In embodiments of the invention, the Lewis acid catalyst content of the carbon/second chlorine source which is supplied to the chlorination zone is about 5000 ppm or less, 2000 ppm or less, about 1000 ppm or less, about 500 ppm or less, about 200 ppm or less, about 100 ppm or less, about 50 ppm or less, about 20 ppm or less or about 10 ppm or less. The Lewis acid type catalysts maybe present from the waste from downstream processes and examples include metal and/or hybrid metal catalysts, e.g. one or more halides (e.g. chlorides, bromides, fluorides or iodides) of transition metals such as iron, aluminium, antimony, lanthanum, tin, titanium, or boron or elements such as sulphur or iodine. Specific examples of catalysts include $FeCl_3$, $AlCl_3$, $SbCl_5$, $SnCl_4$, $TiCl_4$, $BF_3$, $SO_2Cl_2$ and/or metal triflate.

In some embodiment, the iron content of the carbon/second chlorine source which is supplied to the chlorination zone is about 5000 ppm or less, 2000 ppm or less, about 1000 ppm or less, about 500 ppm or less, about 200 ppm or less, about 100 ppm or less, about 50 ppm or less, about 20 ppm or less or about 10 ppm or less.

Additionally or alternatively, in embodiments of the invention, the carbon/second chlorine source may comprise low levels of oxygen containing compounds, for example, at about 5000 ppm or less, 2000 ppm or less, about 1000 ppm or less, about 500 ppm or less, about 200 ppm or less, about 100 ppm or less, about 50 ppm or less, about 20 ppm or less or about 10 ppm or less.

Examples of specific oxygen containing or oxygenated compounds that the present inventors have found to be problematic include chlorinated alcohols, chlorinated alkanols, e.g. tetrachloropropanol, chlorinated acid chlorides e.g. trichloropropanoyl acid chloride, chlorinated carboxylic acids e.g. trichloropropanoic acid, chlorinated aldehydes and chlorinated ketones In embodiments of the invention, the carbon/second chlorine source may comprise is about 5000 ppm or less, 2000 ppm or less, about 1000 ppm or less, about 500 ppm or less, about 200 ppm or less, about 100 ppm or less, about 50 ppm or less, about 20 ppm or less or about 10 ppm or less of any of those compounds. Additionally or alternatively, the carbon/second chlorine source may comprise is about 5000 ppm or less, 2000 ppm or less, about 1000 ppm or less, about 500 ppm or less, about 200 ppm or less, about 100 ppm or less, about 50 ppm or less, about 20 ppm or less or about 10 ppm or less of all of those compounds.

In embodiments of the invention, the carbon/second chlorine source comprises less than about 1000 ppm, less than about 500 ppm, less than about 200 ppm, less than about 100 ppm, less than about 50 ppm or less than about 20 ppm of water.

As will be appreciated by those skilled in the art, chlorinolysis processes typically result in the formation of a product mixture comprising carbon tetrachloride and perchloroethylene. The target ratio of carbon tetrachloride: perchloroethylene that the operator will be aiming to achieve will depend on intended application of the product.

The ratio is governed by chemical equilibrium between carbon tetrachloride and perchloroethylene. In certain prior art disclosures, guidance is provided as to how the process can be modified to provide a degree of control over the ratio. For example, in GB1297392, it is stated that that the preparation of a reaction mixture rich in carbon tetrachloride will favour the formation of perchloroethylene, and vice versa.

Many conventional chlorinolysis processes are developed to produce perchloroethylene in higher amounts than carbon tetrachloride. A number of prior art disclosures alternatively focus on processes with selectivity for carbon tetrachloride. However, selectivity of carbon tetrachloride over perchloroethylene beyond around 70% is challenging. Techniques to maximise carbon tetrachloride concentration include recycling perchloroethylene back into the reactor. However, such a step adds to plant complexity as an additional recycle line is required. Further, this requires the input of additional energy and also increases the formation of unwanted impurities, particularly hexa-chlorinated waste products.

A further advantage of the present invention is that the process can be controlled to deliver repeatably at industrial level, the product mixtures comprising carbon tetrachloride and perchloroethylene at specific target ratios depending on the intended application of that product mixture. In situations where carbon tetrachloride is the principal compound of interest, the process can be operated such that very high selectivity for the production of carbon tetrachloride over perchloroethylene can be achieved, while ensuring also that the hexa-chlorinated waste products are minimised. In embodiments of the invention, and as a result of the use of a partially chlorinated $C_1$ compound, in the process of the present invention carbon tetrachloride:perchloroethylene are produced at a molar ratio of about 1000:1, about 500:1, about 200:1 or about 100:1 to about 50:1, about 20:1, about 10:1 or about 5:1. In embodiments of the invention, where perchloroethylene is also considered to be a product of value, the process can be controlled to produce carbon tetrachloride and perchloroethylene in a more balanced molar ratio, for example in a molar ratio of carbon tetrachloride:perchloroethylene of about 20:1, about 10:1 or about 5:1 to about 3:1, about 2:1 or about 1:1.

As will be appreciated from the disclosure herein, one major advantage of the processes of the present invention is that they permit the re-use of impurity streams which form at various stages of the production of hydrocarbon and chlorinated alkane or chlorinated alkene products. This includes crude product streams comprising carbon tetrachloride from eg WO2016/058566 or similar processes to WO2016/058566 and crude carbon tetrachloride streams that are produced according to the processes of the present invention, if needed. To achieve the effective recovery of chlorine and carbon value, a range of process conditions may be employed, with which the skilled person will be familiar, and/or which are disclosed or exemplified herein. This integrated approach provides highly efficient delivery of selective, high quality chlorinated feedstocks, especially in a continuous mode.

In the process of the present invention, the chlorination zone is operated under conditions necessary to achieve the formation of carbon tetrachloride and optionally perchloroethylene from the starting materials provided in the chlorination zone. The skilled person will be familiar with conditions and apparatus employed in conventional chlorinolysis processes and these may be employed in the processes of the present invention.

In conventional chlorinolysis processes, reactor operating temperatures of around 600° C. are employed. Chlorinolysis reactors are generally operated adiabatically through the use of a coolant, for example a diluent such as carbon tetrachloride or perchloroethylene. Although, in some prior art documents, operating temperatures in the range of 500° C. to 700° C. are mentioned, in the prior art documents discussed above, in all of the exemplified processes, operating temperatures of 590° C. or higher are used.

However, in the advantageous process of the present invention, lower temperatures may be employed to produce carbon tetrachloride. In embodiments of the invention, the operating temperature of the chlorination zone may be maintained within the range of about 400° C. to about 500° C., about 550° C., about 560° C., about 570° C. or about 580° C.

Lower temperatures for the chlorinolysis can be favourably used, resulting in the formation of less hexa-chlorinated impurities.

In embodiments of the invention, the residence time of the reaction mixture in the chlorination zone is at least about 5 seconds, at least about 10 seconds, at least about 15 seconds or at least about 20 seconds.

In embodiments of the invention, the chlorination zone is operated under atmospheric or superatmospheric pressure, i.e. at a pressure greater than about 100 kPa, greater than about 200 kPa, greater than about 300 kPa, greater than about 400 kPa, greater than about 500 kPa, greater than about 600 kPa, greater than about 700 kPa, or greater than about 800 kPa and/or less than about 1500 kPa, about 1200 kPa or about 1000 kPa. Typically higher pressure conditions (e.g. greater than 1000 kPa) would be needed to attain the advantageous conversion rates achievable through use of the present invention. However, as will be appreciated by those skilled in the art, the use of high pressure operations requires higher investment cost and higher risk. Surprisingly, however, as confirmed in the accompanying examples, the processes of the present invention can be operated at lower pressure conditions to surprisingly achieve higher carbon tetrachloride formation and re-utilisation of waste, using more economic industrial plant installation.

A well known drawback of prior art chlorinolysis processes is the formation of impurities, particularly hexa-chlorinated organic compounds. Conventionally, these compounds are formed in an amount of around 1 to 7% by weight of the net product mixture (i.e the amount of carbon tetrachloride and perchloroethylene produced in the chlorination zone). As those skilled in the art will recognise, the most commonly formed hexa-chlorinated impurities comprise hexachlorobenzene, hexachlorobutadiene and hexachloroethane.

The formation of such compounds in these amounts may represent up to about 10% loss of carbon atoms based on total carbon atoms included in the starting materials. Put another way, the yield of carbon atoms (defined as the number of carbon atoms in the carbon tetrachloride and perchloroethylene products as compared to the number of atoms in the feedstocks) is only around 90%.

There is also a substantial loss of the chlorine value, as the byproducts are mainly perchlorinated compounds which cannot be recycled.

In addition to this inefficiency in yield, the extraction of hexa-chlorinated organic impurities from the product mixture as well as their downstream handling and treatment requires the input of extra substantial expense and effort due to their challenging physical and chemical properties (e.g. high melting point, poor solubility in common solvents, toxicity including carcinogenicity, environmentally unfriendly profile, high chemical stability thus slow degradation in nature). Accordingly, minimising in the first place the formation of such problematic impurities would be advantageous, especially fitting with the Stockholm Convention on Persistent Organic Pollutants.

Surprisingly and unexpectedly, use of a $C_1$ chlorinated compound comprising 1 to 3 chlorine atoms results in formation of lower amounts of impurities and a significant increase in production capacity As demonstrated in the accompanying examples, the inventors have found that the process of the present invention can be operated in order to achieve a target molar ratio of carbon tetrachloride:perchloroethylene while simultaneously reducing the formation of problematic impurities, particularly hexa-chlorinated organic compounds. Thus, in embodiments of the invention, the weight ratio of hexa-chlorinated organic compounds: carbon tetrachloride plus perchloroethylene produced in the chlorination zone, i.e. the net product mixture is less than about 2:100, less than about 1.5:100, less than about 1:100, or less than about 0.5:100.

Additionally or alternatively, the content of hexa-chlorinated organic compounds is about 2% or less, about 1.5% or less, about 1% or less or about 0.5% or less by weight of carbon tetrachloride plus perchloroethylene.

Given these reduced levels of hexa-chlorinated organic impurities as compared to products obtained from conventional chlorinolysis processes, the separation and treatment of this limited amount of hexa-chlorinated organic compounds can be economically and safely achieved e.g. by co-incineration (i.e. incineration with other less chlorinated or non-chlorinated hydrocarbon fuels) in an incineration plant for chlorohydrocarbons, as large amounts of any final toxic waste products are not produced, for example during the incineration process.

Additionally, the process of the present invention also advantageously limits the presence of other potentially problematic impurities in the product mixture, for example trichloroethylene, moisture, trichlorobromomethane, phosgene and/or unreacted partially chlorinated $C_1$ compound. In embodiments of the invention, the net product mixture (i.e. carbon tetrachloride plus perchloroethylene produced in the chlorination zone) comprises about 5000 ppm or less, 2000 ppm or less, about 1000 ppm or less, about 500 ppm or less, about 200 ppm or less, about 100 ppm or less, about 50 ppm or less, about 20 ppm or less or about 10 ppm or less of any of those compounds. Additionally or alternatively, the net product mixture may comprise about 5000 ppm or less, 2000 ppm or less, about 1000 ppm or less, about 500 ppm or less, about 200 ppm or less, about 100 ppm or less, about 50 ppm or less, about 20 ppm or less or about 10 ppm or less of all of those compounds.

An advantage of the process of the present invention is that it is capable of proceeding without the need for the addition of a catalyst. Thus, in embodiments of the present invention, no catalyst is provided to the chlorination zone.

In embodiments of the invention, chlorine, the carbon/second chlorine source and/or the $C_1$ chlorinated compound comprising 1 to 3 chlorine atoms may be fed into the chlorination zone either continuously or intermittently. The chlorination zone may be fed with one or more feeds of those starting materials.

The amount of chlorine provided to the chlorination zone is preferably in stoichiometric excess: the term 'stoichiometric excess' refers to any amount of chlorine above the overall reaction stoichiometry, introduced into the reaction zone in any form, i.e. free molecular chlorine as well as chlorine bonded in the molecules, which results in unreacted molecular chlorine surplus (content) in the reaction mixture leaving the reaction zone under the conditions of the reaction zone. This chlorine excess will depend on the make up of the feed going into the reactor and the chlorine calculation will account for both the free chlorine introduced and the chlorine available via the chlorinated feed. In embodiments of the invention, the stoichiometric molar excess or surplus of chlorine is at least about 5%, 10%, 20%, 30%, 40%, or 50%. For the avoidance of doubt, where reference is made herein to the stoichiometric molar excess being 'at least about' a specific amount, this means that the number of moles of chlorine present meets the numerical requirement at least, but a greater amount of chlorine may also be present.

The chlorine used as a starting material in the processes of the present invention is preferably highly pure. In embodiments of the invention, the chlorine fed into the reaction zone/s employed at any stage in the present invention preferably has a purity of at least about 95%, at least about 97%, at least about 99%, at least about 99.5%, or at least about 99.9%

Additionally or alternatively, the chlorine used in the processes of the present invention may comprise bromine in an amount of about 200 ppm or less, about 100 ppm or less, about 50 ppm or less, about 20 ppm or less or about 10 ppm or less.

The use of chlorine gas comprising low amounts of oxygen (e.g. about 2000 ppmv, 1500 ppmv, 1000 ppmv, 500 ppmv, 200 ppmv or less, about 100 ppmv or less, about 50 ppmv or less, about 20 ppmv or less or about 10 ppmv or less) is also envisaged. Both evaporated and compressed chlorine gas can be mixed prior to entry to chlorination zone. In embodiments of the invention, evaporated chlorine with very low oxygen content is preferred.

In embodiments of the invention, the chlorine employed in the processes of the invention can come from a chloro-alkali plant, chloro-alkali electrolysis, hydrochloric acid electrolysis membrane and diaphragm plant.

In embodiments of the invention, a stoichiometric excess of chlorine is provided into the chlorination zone: the term 'stoichiometric excess' is defined above.

One advantage of the processes of the present invention is that desirous results are obtained when the chlorination zone is operated in continuous mode. The terms 'continuous mode' and 'continuous process' will be understood by those skilled in the art.

The chlorination zone may be provided in any reactor known to those skilled in the art as being suitable for conducting chlorinolysis reactions. In embodiments of the invention, the reactor is a gas phase, high temperature adiabatic or semi-adiabatic reactor.

The adiabatic condition may be without heat removal or may be semi-adiabatic or isothermic both with heat removal. Any type of reactor design may be employed, including tubular with or without back mixing with a different flow pattern.

The reactor in which the chlorination zone is present may be manufactured from an appropriate material of construction which is resistant towards corrosion as the mixtures to which it is exposed include free chlorine and the reaction is operated at high temperatures. One example of reactor design is to have a reactor with brick lining and shell external cooling or a reactor formed of various nickel based alloys or nickel itself with shell external cooling.

In processes of the present invention, it is generally desirable to rapidly cool or quench the product mixture extracted from the chlorination zone in order to stop reactions. Quenching by cold liquid is a common method.

Additionally or alternatively, a quench column may be located downstream of the chlorination zone.

The composition of product mixture may be determined as soon as is practicable following extraction of the product mixture from the chlorination zone. For example, a sample of product mixture may be extracted at a point adjacent to or slightly downstream of the outlet of the chlorination zone.

To obtain highly pure carbon tetrachloride and/or perchloroethylene, one or more subsequent treatment steps may be performed.

In embodiments of the invention, the product mixture may be subjected to one or more distillation steps. If performed, streams rich in (e.g. which comprise at least about 50%, at least about 60%, at least about 70%, at least about 80%, at least about 90%, at least about 95%, at least about 97%, at least about 98%, at least about 99%, at least about 99.5%, at least about 99.7%, at least about 99.8% or at least about 99.9%, or at least 99.95% and 99.99% by weight of) carbon tetrachloride and/or perchloroethylene may be obtained from such distillation step/s.

Any distillation apparatus may be employed in the processes of the present invention. In embodiments of the invention, the distillation apparatus may comprise one, two, three, four, five or more distillation and/or rectification columns. Where a plurality of distillation and/or rectification columns are employed, these may be operated sequentially or in parallel.

For example, two major distillation columns may be employed: the first distillation column separates pure carbon tetrachloride from crude perchloroethylene, which crude perchloroethylene is then passed to the second column which separates purified perchloroethylene from heavies.

In embodiments of the invention, carbon tetrachloride distillate may be treated to remove trace amounts of chlorine. In embodiments of the invention, carbon tetrachloride distillate is washed, for example using aqueous sodium hydroxide and dried.

The processes of the present invention enable the production of high quality (e.g. having a purity of at least about 99.95% or 99.99% by weight), and efficiently produced carbon tetrachloride with an impurity profile which is highly controlled. Advantageously, the process of the present invention prevents or retards the formation of impurities including those which otherwise would be challenging to remove. This attractive impurity profile means that the product obtained from the process of the present invention is desirable as a feedstock for use in a wide range of downstream reactions.

For the avoidance of doubt, where reference is made herein to a carbon tetrachloride product, distillate or the like (or product, distillate or the like of any other compound), this does not mean that the product, distillate or the like contains only carbon tetrachloride (of the other product). Such product, distillate or the like is a composition that comprises carbon tetrachloride (or the other product) present as its principal constituent and optionally other compounds present.

Carbon tetrachloride products, with high purity, that are obtainable as products of the present invention are useful as feedstocks in downstream processes, such as telomerisation reactions, chlorination reactions (e.g. those using UV and/or metal catalysts), and/or dehydrochlorination reactions (e.g. those using metal catalysts). Through the use of the products of the present invention, which have high purity and controlled impurity profiles, downstream processes employing those products as feedstocks can be used to obtain final target compounds themselves with very low impurities.

As an example of impurities in carbon tetrachloride compositions that can be problematic in downstream telomerisation reactions (such as those disclosed in WO2016/058566, and WO2016/058569) include trichloroethylene, perchloroethylene, bromotrichloromethane and water. For example, if carbon tetrachloride used as a feedstock in the telomerisation of ethylene and carbon tetrachloride comprises 1 wt % of trichloroethylene, the reaction proceeds at such a low rate of conversion that the process is commercially non-viable.

In embodiments of the invention, the composition obtained from the process of the present invention may be liquid and may comprise:

about 99.0% or more, about 99.5% or more, about 99.7% or more, about 99.8% or more or about 99.9% or more or about 99.95% or more of the carbon tetrachloride, and less than about 2000 ppm, less than about 1000 ppm, less than about 500 ppm, less than about 200 ppm or less than about 100 ppm chlorinated alkane impurities (i.e. chlorinated alkane compounds other than carbon tetrachloride), less than about 2000 ppm, less than about 1000 ppm, less than about 500 ppm, less than about 200 ppm or less than about 100 ppm chlorinated alkene compounds, less than about 2000 ppm, less than about 1000 ppm, less than about 500 ppm, less than about 200 ppm or less than about 100 ppm oxygenated organic compounds, less than about 2000 ppm, less than about 1000 ppm, less than about 500 ppm, less than about 200 ppm or less than about 100 ppm brominated compounds, less than about 500 ppm, less than about 200 ppm, less than about 100 ppm, less than about 50 ppm or less than about 20 ppm of water, less than about 500 ppm, less than about 200 ppm, less than about 100 ppm, less than about 50 ppm or less than about 20 ppm of trichloroethene and/or tetrachloroethene, less than about 500 ppm, less than about 200 ppm, less than about 100 ppm, less than about 50 ppm or less than about 20 ppm of hexa-chlorinated impurities, and/or less than about 500 ppm, less than about 200 ppm, less than about 100 ppm, less than about 50 ppm or less than about 20 ppm of unreacted $C_1$ chlorinated compound comprising 1 to 3 chlorine atoms starting material.

The prior art fails to disclose or teach processes for producing carbon tetrachloride having such a high degree of purity and in high yield, with selective reaction. Thus, according to a further aspect of the present invention, there is provided a high purity carbon tetrachloride composition as set out above.

Additionally, the compositions as outlined above have impurity profiles which make them especially well suited to use as starting materials in the synthesis of a wide range of downstream compounds, including $C_{3-6}$ compounds such as chlorinated $C_{3-4}$ alkanes and alkenes, e.g. pentachloropropanes and tetrachloropropenes, such as 240db, 240fa, 250fb, 1240za, 1230xa, 1230za, and which chlorinated compounds are feedstocks for production of target fluoroalkanes e.g. 245fa, fluoroalkenes, e.g. 1234yf, 1234ze, and/or fluorochloroalkenes, e.g. 1233xf, 1233zd. Such target compounds may find utility as (or in the preparation of) fluoropolymers, refrigerants, blowing agents, de-greasing agents and/or catalyst recovery agents. Thus, according to a further aspect of the present invention, there is provided the use of the compositions outlined herein as feedstocks in the synthesis of the above-identified compounds.

In processes of the present invention, where the compositions outlined above, or which are obtained from the processes of the present invention, are used as feedstocks in the production of downstream compounds via downstream process steps, advantageously, waste product streams produced in those downstream process steps can be recycled back to the chlorination zone such that the waste product streams can serve as the carbon/second chlorine source.

The processes of the present invention are particularly advantageous as it enables highly pure chlorinated alkanes to be produced using simple and straightforward techniques and equipment with which one skilled in the art would be familiar.

In accordance with a further aspect of the present invention, there is provided a process in which carbon tetrachloride which is obtained as a product of the processes discussed herein, or which is provided in a composition disclosed herein is reacted with ethylene to obtain a chlorinated alkane, for example 1,1,1,3-tetrachloropropane. Examples of the techniques and apparatus that may be employed in such a reaction are disclosed in WO2016/058566 or WO2016/058569.

Thus, in embodiments of the invention, the following steps may be performed:

the chlorination zone is operated at a temperature of less 550° C. to produce a carbon tetrachloride composition having a purity greater than 99.9%;

the process includes a further step of reacting a carbon tetrachloride composition (as discussed above, which may be obtained from the processes discussed herein) with an alkene using metal and organophosphate catalyst to produce a first chlorinated alkane;

the first chlorinated alkane is reacted with chlorine in a reaction zone, where the amount of chlorine provided to the reaction zone is substoichiometric as compared to the amount of first chlorinated alkane to produce a second chlorinated alkane;

wherein the impurity streams generated in the production of the first and/or second chlorinated alkane are recycled back to the chlorination zone and are employed in the process of the invention as the carbon/second chlorine source in the production of carbon tetrachloride.

According to a further aspect of the invention, there is provided a process in which a highly pure carbon tetrachloride composition is prepared via a chlorinolysis reaction, operated at a temperature of equal to or less than about 570° C. with a stoichiometric excess of chlorine such that there is unreacted chlorine at the outlet of the reactor, the highly pure carbon tetrachloride composition comprising minor amounts of impurities having a boiling point which differs from the boiling point of carbon tetrachloride by 10° C. or less ("close boiling impurities");

the carbon tetrachloride composition is employed as a feedstock in a subsequent reaction step in which the carbon tetrachloride is reacted with an alkene using metal and organophosphate catalyst to produce a first chlorinated alkane of interest (e.g. 1,1,1,3-tetrachloropropane), wherein unreacted carbon tetrachloride with close boiling points impurities is recycled back and used as a feedstock in the chlorinolysis reaction; and reacting the first chlorinated alkane with Lewis acid to form a first chlorinated alkene (e.g. 1,1,3-trichloropropene)

with isomeric selectivity greater than 99% (e.g. favouring the formation of 1,1,3-trichloropropene over 3,3,3-trichloropropene);

reacting the first chlorinated alkene with a substoichiometric amount of chlorine in the presence of UV/visible light to produce a second chlorinated alkane (e.g. 1,1,1,2,3-pentachloropropane) with isomeric selectivity greater than 99% (e.g. favouring the formation of 1,1,1,2,3-pentachloropropane over the 1,1,1,3,3-pentachloropropane);

purifying the second chlorinated alkane to produce a composition comprising the second chlorinated alkane (e.g. 1,1,1,2,3-pentachloropropane) having a purity of about 99.9% or more (e.g. about 99.95% or more, with low levels of oxygenated organic compounds, brominated organic compounds, metals, moisture and/or acidity); and optionally using the purified second chlorinated alkane as a feedstock in the production of 1234yf, 1234ze, 1233xf, and/or 1233zd; or reacting the first chlorinated alkene with a substoichiometric amount of chlorine, optionally in the presence of UV/visible light and/or Lewis acid catalyst to produce a third chlorinated alkane or a mixture of chlorinated alkanes (e.g. 1,1,1,3,3-pentachloropropane and 1,1,1,2,3-pentachloropropane) in a molar ratio of from about 80:20 to about 5:95;

reacting the mixture of chlorinated alkanes of interest with a Lewis acid to produce a first corresponding chlorinated alkene (1,1,3,3-tetrachloropropene) and one unreacted chlorinated alkane (e.g. 1,1,1,2,3-pentachloropropane);

purifying the first corresponding chlorinated alkene (e.g. 1,1,3,3-tetrachloropropene) to achieve a minimum purity of 99.0% (e.g. a purity of 99.9% with low amounts of impurities, such as oxygenated organic compounds, brominated organic compounds, metals, moisture, acidity). The purified first chlorinated alkene may then be used as a feedstock in the preparation of 1233zd, and/or 1234ze;

purifying the one unreacted chlorinated alkane (e.g. 1,1,1,2,3-pentachloropropane) to achieve a minimum purity of 99.9% (e.g. a purity of 99.95% with low amounts of impurities, such as oxygenated organic compounds, brominated organic compounds, metals, moisture or acidity). The purified unreacted chlorinated alkane may be used as feedstock in the preparation of 1234yf, 1234ze, and/or 1233xf;

reacting the purified unreacted chlorinated alkane with Lewis acid to produce a corresponding chlorinated alkene (e.g. 1,1,2,3-tetrachloropropene).

purifying the corresponding chlorinated alkene (e.g. 1,1,2,3-tetrachloropropene) to achieve a purity level of 99.5% or more (e.g. a purity of 99.9% with low amounts of impurities, such as oxygenated organic compounds, brominated organic compounds, metals, moisture, acidity or 1,1,3,3-tetrachloropropene). The purified corresponding chlorinated alkene may be used as a feedstock in the preparation of 1234yf, and/or 1233xf;

wherein the impurity streams from any, some or all of these steps are fed back into the chlorination zone used in the chlorinolysis step to produce carbon tetrachloride.

The present invention will now be further illustrated by the following examples.

| 1 | fresh chlorine gas feedstream |
| 2 | gaseous propylene feedstream |
| 3 | waste hydrocarbon feedstream |
| 4 | alternative liquid feedstream |
| 5 | gas phase high temperature semi-adiabatic reactor |
| 6 | reactor outlet |
| 7 | quench column |
| 8 | intermediate line |
| 9 | first evaporator to concentrate the heavy ends |
| 10 | first evaporator vapor-phase outlet |
| 11 | intermediate line |
| 12 | second evaporator to concentrate the heavy ends |
| 13 | heavy ends (hexa-chlorinated organic impurities) |
| 14 | second evaporator vapor-phase outlet |
| 15 | crude product mixture |
| 16 | quench column overhead vapor stream |
| 17 | quench column overhead first partial condenser |
| 18 | intermediate line |
| 19 | first partial condenser vapor-liquid separator |
| 20 | first liquid condensate |
| 21 | intermediate line |
| 22 | quench column overhead second partial condenser |
| 23 | intermediate line |
| 24 | second partial condenser vapor-liquid separator |
| 25 | second liquid condensate |
| 26 | intermediate line |
| 27 | quench column overhead third partial condenser |
| 28 | intermediate line |
| 29 | third partial condenser vapor-liquid separator |
| 30 | third liquid condensate |
| 31 | intermediate line after condensation |
| 32 | sum of condensates |
| 33 | sum of condensates |
| 34 | quench column reflux stream |
| 35 | CTC liquid diluent |
| 36 | CTC liquid stream for vaporization |
| 37 | liquid chloroform stream for vaporization |
| 38 | gaseous diluent evaporator |
| 39 | gaseous diluent |
| 40 | hydrogen chloride absorption unit |
| 41 | 32% hydrochloric acid |
| 42 | water or weak hydrochloric acid |
| 43 | unreacted wet chlorine stream |
| 44 | system for drying/recycling the unreacted chlorine |
| 45 | spent sulphuric acid |
| 46 | concentrated sulphuric acid |
| 47 | dry chlorine gas |
| 48 | chlorine compressor |
| 49 | recycled chlorine gas stream |
| 50 | recycled perchloroethylene from distillation unit |

ABBREVIATIONS USED

| CTC | Carbon Tetrachloride, Tetrachloromethane |
| PER | Perchloroethylene, Tetrachloroethylene |
| CHM | Chloroform, Trichloromethane |
| TCE | Trichloroethene |
| CHCE | Hexachloroethane |
| HCBu | Hexachlorobutadiene |
| PCB | Pentachlorobenzene |
| HCB | Hexachlorobenezene |
| X | Un-identified remainder |

EXAMPLES

Five comparative examples and four inventive examples which detail the preparation of carbon tetrachloride and perchloroethylene via chlorinolysis are provided herein. Table 1 at the end of the examples section presents, in tabular form, full details of the parameters employed in those examples.

Comparative Example 1

Figure 1:
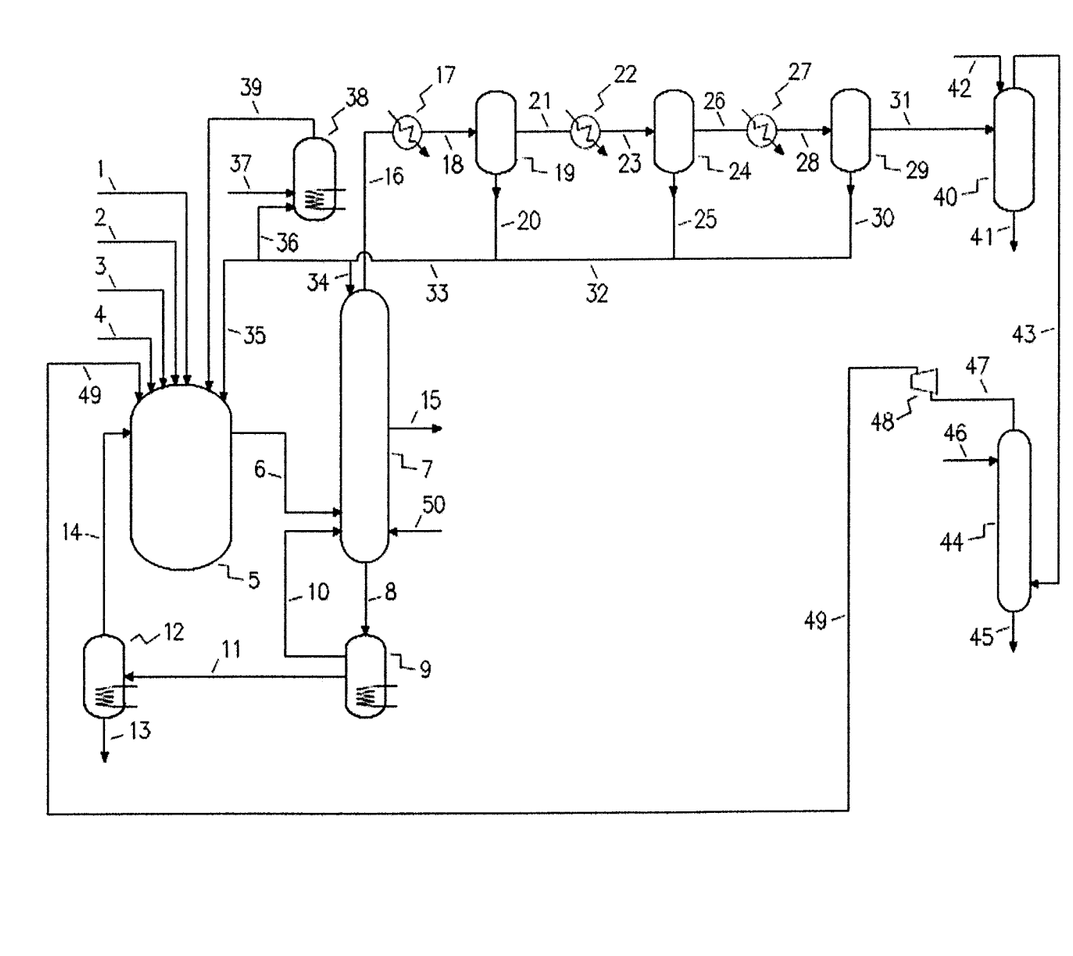
FIG. 1—High Temperature Chlorinolysis Unit

Chlorinolysis apparatus was set up as shown in FIG. 1. The chlorination zone is provided in a reaction unit which consists of a gas phase high temperature semi-adiabatic (cooled shell) reactor 5 operated at a pressure of about 194 kPa (0.94 BARg), with a quench column 7. The quench column has a system of overheads for partial condensation 17, 19, 22, 24, 27, 29, a system to concentrate heavies 9, 12, a system to withdraw crude product 15, a system for HCl absorption 40 and a system for drying/recycling unreacted chlorine 44, 48. For simplicity, not all devices are illustrated. For example, the distillation apparatus to produce the final products, accumulation tanks etc. are not shown.

Fresh chlorine gas (obtained by evaporating liquid chlorine) was fed into the reactor 5 via line 1 at a rate of 3048 kg/h. Recycled chlorine was fed in to the reactor 5 via line 49 at a rate of 536 kg/h. Gaseous propylene was fed into the reactor 5 via line 2 at a rate of 230 kg/h. A waste hydrocarbon stream, comprising principally 1,2-dichloropropane and cis and trans 1,3-dichloropropene were fed into the reactor 5 at a rate of 278 kg/h via line 3.

Gaseous diluent was fed via line 39 at a rate of 4037 kg/h and liquid diluent was fed via line 35 at a rate of 1211 kg/h into the reactor. The diluent streams both comprised 94.5% carbon tetrachloride and 5% perchloroethylene by weight in order to control temperature and the molar ratio of carbon tetrachloride:perchloroethylene in the reactor 5. A further liquid diluent (recycled carbon tetrachloride having a purity of 99.9%, separated from the crude product mixture by distillation) was fed into the reactor 5 at a rate of 612 kg/h via line 4.

Perchloroethylene (separated from the crude product mixture and having a purity of 95.3% and additionally comprising 2.6% hexachloroethane and 1.6% hexachlorobutadiene and some hexachlorobenzene) was fed into the quench column 7 at a rate of 690 kg/h via line 50.

The temperature at the reactor was 585° C. and the average content of unreacted chlorine in line 31 was 11% by volume.

The crude product mixture was extracted from the quench column on a continuous basis at a rate of 3132 kg/h via line 15. The crude product mixture comprised 21% carbon tetrachloride and 78% perchloroethylene. Thus the extraction rate for each compound was 661 kg/h for carbon tetrachloride and 2456 kg/h for perchloroethylene.

The net production flow rate of carbon tetrachloride at unit battery limit (excluding recycled carbon tetrachloride in line 4) was 49 kg/h and the net production flow rate of perchloroethylene at unit battery limit (excluding recycled perchloroethylene in line 50) was 1781 kg/h.

The crude product mixture was then distilled using distillation apparatus comprising two continuously operated rectification columns. Carbon tetrachloride was obtained at a purity of 99.97% with a content of 82 ppm chloroform and perchloroethylene was obtained at a purity of 99.98%.

As a byproduct of the reaction, hydrogen chloride was extracted at a rate of 1421 kg/h. After absorption 40 into water, 32% hydrochloric acid was extracted via line 41 at a rate of about 4439 kg/h.

Heavy ends were extracted via line 13 at a rate of around 133 kg/h. The contents of that stream was analysed (Table 3) and it was found to principally comprise hexachlorobenzene, hexachlorobutadiene and hexachloroethane. This equated to a production of 7.32% of those compounds, based on the weight of the net produced carbon tetrachloride and perchloroethylene.

Comparative Example 2

The reaction unit was set up in the same way as described above in Comparative Example 1. This comparative example represents a designed nominal values.

Fresh chlorine gas (obtained by evaporating liquid chlorine) was fed into the reactor 5 via line 1 at a rate of 4344 kg/h. Recycled chlorine was fed in to the reactor 5 via line 49 at a rate of 851 kg/h. Gaseous propylene was fed into the reactor 5 via line 2 at a rate of 409 kg/h.

Gaseous diluent (97.8% carbon tetrachloride, 1% perchloroethylene) was fed via line 39 at a rate of 12019 kg/h in order to control temperature and the molar ratio of carbon tetrachloride:perchloroethylene in the reactor 5. No liquid diluent was fed into the reactor 5.

Perchloroethylene (separated from the crude product mixture, with purity of 78% and additionally comprising 22% hexachloroethane) was fed into the quench column 7 at a rate of 685 kg/h via line 50.

The temperature at the reactor was 585° C. and the average content of unreacted chlorine in line 31 was 16% by volume.

The crude product mixture was extracted from the quench column on a continuous basis at a rate of 3236 kg/h via line 15. The crude product mixture comprised 16.8% carbon tetrachloride, 78.7% perchloroethylene and 4.2% hexachloroethane. Thus the extraction rate for each compound was 543 kg/h for carbon tetrachloride and 2547 kg/h for perchloroethylene.

The net production flow rate of carbon tetrachloride at unit battery limit was 500 kg/h and the net production flow rate of perchloroethylene at unit battery limit (excluding recycled perchloroethylene in line 50) was 2000 kg/h.

The crude product mixture was then distilled using distillation apparatus comprising two continuously operated rectification columns. Carbon tetrachloride was obtained at a purity of 100% and perchloroethylene was obtained at a purity of 100%, as judged by the original Stauffer test protocols.

As a byproduct of the reaction, hydrogen chloride was extracted at a rate of 2156 kg/h. After absorption 40 into water, 32% hydrochloric acid was extracted via line 41 at a rate of about 6738 kg/h.

Heavy ends were extracted via line 13 at a rate of around 93.1 kg/h. The contents of that stream was analysed (Table 3) and it was found to principally comprise hexachlorobenzene, hexachlorobutadiene and hexachloroethane. This equated to a production of 3.72% of those compounds, based on the weight of the net carbon tetrachloride and perchloroethylene produced in the chlorination zone.

Comparative Example 3

The reaction unit was set up in the same way as described above in Comparative Example 1.

Fresh chlorine gas (obtained by evaporating liquid chlorine) was fed into the reactor 5 via line 1 at a rate of 3000 kg/h. Recycled chlorine was fed in to the reactor 5 via line 49 at a rate of 1351 kg/h. Gaseous propylene was fed into the reactor 5 via line 2 at a rate of 255 kg/h.

Gaseous diluent was fed via line 39 at a rate of 3900 kg/h and liquid diluent was fed via line 35 at a rate of 1597 kg/h into the reactor. The diluent streams both comprised 99.6% carbon tetrachloride and 0.3% perchloroethylene by weight in order to control temperature and the molar ratio of carbon tetrachloride:perchloroethylene in the reactor 5.

The temperature at the reactor was 540° C. and the average content of unreacted chlorine in line 31 was 25.9% by volume.

The crude product mixture was extracted from the quench column on a continuous basis at a rate of 1890 kg/h via line 15. The crude product mixture comprised 50.1% carbon tetrachloride, 48.8% perchloroethylene and 0.9% hexachloroethane. Thus the extraction rate for each compound was 947 kg/h for carbon tetrachloride and 922 kg/h for perchloroethylene.

Net production rate after correction on accumulation was then 956 kg/h for carbon tetrachloride and 911 kg/h for perchloroethylene.

The crude product mixture was then distilled using distillation apparatus comprising two continuously operated rectification columns.

As a byproduct of the reaction, hydrogen chloride was extracted at a rate of 1365 kg/h. After absorption 40 into water, 32% hydrochloric acid was extracted via line 41 at a rate of about 4266 kg/h.

Heavy ends were extracted via line 13 at a rate of around 18.7 kg/h. The contents of that stream was analysed (Table 3) and it was found to principally comprise hexachlorobenzene, hexachlorobutadiene and hexachloroethane. This equated to a production of 1.00% of those compounds, based on the weight of the net carbon tetrachloride and perchloroethylene produced in the chlorination zone.

Comparative Example 4

The reaction unit was set up in the same way as described above in Comparative Example 1.

Fresh chlorine gas (obtained by evaporating liquid chlorine) was fed into the reactor 5 via line 1 at a rate of 2843 kg/h. Recycled chlorine was fed in to the reactor 5 via line 49 at a rate of 1282 kg/h. Gaseous propylene was fed into the reactor 5 via line 2 at a rate of 239 kg/h.

Gaseous diluent (99.4% carbon tetrachloride and 0.6% perchloroethylene) was fed via line 39 at a rate of 2000 kg/h and liquid diluent (99.4% carbon tetrachloride and 0.6% perchloroethylene) was fed via line 35 at a rate of 1518 kg/h into the reactor 5.

The diluent streams were added in order to control temperature and the molar ratio of carbon tetrachloride: perchloroethylene in the reactor 5.

A further liquid external recycle (perchloroethylene 98.2% and 1.8% carbon tetrachloride, recycled from distillation apparatus) was fed into the reactor 5 at a rate of 667 kg/h via line 4.

The temperature at the reactor was 540° C. and the average content of unreacted chlorine in line 31 was 26.3% by volume.

The crude product mixture was extracted from the quench column on a continuous basis at a rate of 2491 kg/h via line 15. The crude product mixture comprised 42.0% carbon tetrachloride, 56.8% perchloroethylene and 0.9% hexachloroethane. Thus the extraction rate for each compound was 1046 kg/h for carbon tetrachloride and 1415 kg/h for perchloroethylene.

Net production rate after correction on accumulation was then 1065 kg/h for carbon tetrachloride and 730 kg/h for perchloroethylene. (i.e. excluding recycled perchloroethylene from line 4).

The crude product mixture was then distilled using distillation apparatus comprising two continuously operated rectification columns. Carbon tetrachloride was obtained at a purity of 99.99% with a content of 31 ppm chloroform As a byproduct of the reaction, hydrogen chloride was extracted at a rate of 1258 kg/h. After absorption 40 into water, 32% hydrochloric acid was extracted via line 41 at a rate of about 3931 kg/h.

Heavy ends were extracted via line 13 at a rate of around 21.0 kg/h. The contents of that stream was analysed (Table 3) and it was found to principally comprise hexachlorobenzene, hexachlorobutadiene and hexachloroethane. This equated to a production of 1.17% of those compounds, based on the weight of the net carbon tetrachloride and perchloroethylene produced in the chlorination zone.

Comparative Example 5

The reaction unit was set up in the same way as described above in Comparative Example 1.

Fresh chlorine gas (obtained by evaporating liquid chlorine) was fed into the reactor 5 via line 1 at a rate of 3079 kg/h. Recycled chlorine was fed in to the reactor 5 via line 49 at a rate of 1230 kg/h. Gaseous propylene was fed into the reactor 5 via line 2 at a rate of 228 kg/h.

Gaseous diluent (99.1% carbon tetrachloride and 0.9% perchloroethylene) was fed via line 39 at a rate of 1949 kg/h into the reactor 5. The diluent stream was added to control temperature and the molar ratio of carbon tetrachloride: perchloroethylene in the reactor 5.

A further liquid external recycle (perchloroethylene 99.8% and 0.2% carbon tetrachloride, recycled from distillation apparatus) was fed into the reactor 5 at a rate of 971 kg/h via line 4.

The temperature at the reactor was 560° C. and the average content of unreacted chlorine in line 31 was 26.1% by volume.

The crude product mixture was extracted from the quench column on a continuous basis at a rate of 3062 kg/h via line 15. The crude product mixture comprised 43.7% carbon tetrachloride, 55.9% perchloroethylene and 0.3% hexachloroethane. Thus the extraction rate for each compound was 1338 kg/h for carbon tetrachloride and 1712 kg/h for perchloroethylene.

Net production rate after correction on accumulation was then 1335 kg/h for carbon tetrachloride and 740 kg/h for perchloroethylene (i.e. excluding recycled perchloroethylene from line 4).

The crude product mixture was then distilled using distillation apparatus comprising two continuously operated rectification columns. Carbon tetrachloride was obtained at a purity of 99.99% with a content of 56 ppm chloroform.

As a byproduct of the reaction, hydrogen chloride was extracted at a rate of 1216 kg/h. After absorption 40 into water, 32% hydrochloric acid was extracted via line 41 at a rate of about 3800 kg/h.

Heavy ends were extracted via line 13 at a rate of around 37.6 kg/h. The contents of that stream was analysed (Table 3) and it was found to principally comprise hexachlorobenzene, hexachlorobutadiene and hexachloroethane. This equated to a production of 1.81% of those compounds, based on the weight of the net carbon tetrachloride and perchloroethylene produced in the chlorination zone.

Example 1

The reaction unit was set up in the same way as described above in Comparative Example 1.

Fresh chlorine gas (obtained by evaporating liquid chlorine) was fed into the reactor 5 via line 1 at a rate of 3066 kg/h. Recycled chlorine was fed in to the reactor 5 via line 49 at a rate of 1265 kg/h. Gaseous propylene was fed into the reactor 5 via line 2 at a rate of 202 kg/h.

Chloroform feedstock with 99.9% purity additionally comprising 50 ppm moisture and 20 ppm of amylene was fed via line 37 to the evaporator 38 and then as a gaseous diluent via line 39 at a rate of 1023 kg/h into the reactor 5. A second gaseous diluent (vapourised carbon tetrachloride 99.9% and perchloroethylene 0.1%) was fed into the reactor 5 via line 36 and 39 at a rate of 975 kg/h. Additionally, a liquid diluent (carbon tetrachloride 99.9% and perchloroethylene 0.1%) was fed into the reactor 5 via line 35 at a feed rate of 1107 kg/h. The diluent streams were added to control temperature and the molar ratio of carbon tetrachloride:perchloroethylene in the reactor 5.

The temperature at the reactor was 540° C. and the average content of unreacted chlorine in line 31 was 29.5% by volume.

The crude product mixture was extracted from the quench column on a continuous basis at a rate of 2983 kg/h via line 15. The crude product mixture comprised 72.6% carbon tetrachloride, 27.2% perchloroethylene and 0.1% hexachloroethane. Thus the extraction rate for each compound was 2166 kg/h for carbon tetrachloride and 811 kg/h for perchloroethylene. As can be seen, the selectivity of this process towards carbon tetrachloride over perchloroethylene was far higher than in the comparative examples above.

Net production rate after correction on accumulation was then 2166 kg/h for carbon tetrachloride and 808 kg/h for perchloroethylene.

The crude product mixture was then distilled using distillation apparatus comprising two continuously operated rectification columns. Carbon tetrachloride was obtained at a purity of 99.98%, with a content of less than 100 ppm chloroform.

As a byproduct of the reaction, hydrogen chloride was extracted at a rate of 1308 kg/h. After absorption 40 into water, 32% hydrochloric acid was extracted via line 41 at a rate of about 4088 kg/h.

Heavy ends were extracted via line 13 at a rate of around 9.2 kg/h. The contents of that stream was analysed (Table 3) and it was found to principally comprise hexachlorobenzene, hexachlorobutadiene and hexachloroethane. This equated to a production of 0.31% of those compounds, based on the weight of the net carbon tetrachloride and perchloroethylene produced in the chlorination zone. This is a significantly lower proportion of hexa-chlorinated organic impurities than were formed in the comparative examples Example 2

The reaction unit was set up in the same way as described above in Comparative Example 1.

Fresh chlorine gas (obtained by evaporating liquid chlorine) was fed into the reactor 5 via line 1 at a rate of 3322 kg/h. Recycled chlorine was fed in to the reactor 5 via line 49 at a rate of 1278 kg/h. Gaseous propylene was fed into the reactor 5 via line 2 at a rate of 199 kg/h.

Chloroform feedstock with 99.9% purity additionally comprising 50 ppm moisture and 20 ppm of amylene was fed via line 37 to the evaporator 38 and then as a gaseous diluent via line 39 at a rate of 1362 kg/h into the reactor 5. A second gaseous diluent (vapourised carbon tetrachloride 99.94% and perchloroethylene 0.05%) was fed into the reactor 5 via line 36 and 39 at a rate of 412 kg/h. Additionally, a liquid diluent (carbon tetrachloride 99.94% and perchloroethylene 0.05%) was fed into the reactor 5 via line 35 at a feed rate of 1593 kg/h. The diluent streams were added to control temperature and the molar ratio of carbon tetrachloride:perchloroethylene in the reactor 5.

The temperature at the reactor was 540° C. and the average content of unreacted chlorine in line 31 was 25.4% by volume.

The crude product mixture was extracted from the quench column on a continuous basis at a rate of 3455 kg/h via line 15. The crude product mixture comprised 76.4% carbon tetrachloride, 23.4% perchloroethylene and 0.1% hexachloroethane. Thus the extraction rate for each compound was 2640 kg/h for carbon tetrachloride and 808 kg/h for perchloroethylene. As can be seen, the selectivity of this process towards carbon tetrachloride over perchloroethylene was far higher than in the comparative examples above.

Net production rate after correction on accumulation was then 2639 kg/h for carbon tetrachloride and 806 kg/h for perchloroethylene.

The crude product mixture was then distilled using distillation apparatus comprising two continuously operated rectification columns. Carbon tetrachloride was obtained at a purity of 99.97%, with a content of less than 100 ppm chloroform.

As a byproduct of the reaction, hydrogen chloride was extracted at a rate of 1428 kg/h. After absorption 40 into water, 32% hydrochloric acid was extracted via line 41 at a rate of about 4463 kg/h.

Heavy ends were extracted via line 13 at a rate of around 23.1 kg/h. The contents of that stream was analysed (Table 3) and it was found to principally comprise hexachlorobenzene, hexachlorobutadiene and hexachloroethane. This equated to the production of 0.67% of those compounds, based on the weight of the net carbon tetrachloride and perchloroethylene produced in the chlorination zone. This is a significantly lower proportion of hexa-chlorinated organic impurities than were formed in the comparative examples Example 3

The reaction unit was set up in the same way as described above in Comparative Example 1.

Fresh chlorine gas (obtained by evaporating liquid chlorine) was fed into the reactor 5 via line 1 at a rate of 3480 kg/h. Recycled chlorine was fed in to the reactor 5 via line 49 at a rate of 1044 kg/h. Gaseous propylene was fed into the reactor 5 via line 2 at a rate of 199 kg/h.

Chloroform feedstock with 99.9% purity additionally comprising 50 ppm moisture and 20 ppm of amylene was fed via line 37 to the evaporator 38 and then as a gaseous diluent via line 39 at a rate of 1867 kg/h into the reactor 5. A second gaseous diluent (vapourised carbon tetrachloride 99.8% and perchloroethylene 0.0%) was fed into the reactor 5 via line 36 and 39 at a rate of 343 kg/h. Additionally, a liquid diluent (carbon tetrachloride 99.8% and perchloroethylene 0.0%) was fed into the reactor 5 via line 35 at a feed rate of 2077 kg/h. The diluent streams were added to control temperature and the molar ratio of carbon tetrachloride:perchloroethylene in the reactor 5.

The temperature at the reactor was 540° C. and the average content of unreacted chlorine in line 31 was 19.8% by volume.

The crude product mixture was extracted from the quench column on a continuous basis at a rate of 4071 kg/h via line 15. The crude product mixture comprised 80.9% carbon tetrachloride, 18.7% perchloroethylene and 0.3% hexachloroethane. Thus the extraction rate for each compound was 3293 kg/h for carbon tetrachloride and 761 kg/h for perchloroethylene. As can be seen, the selectivity of this process towards carbon tetrachloride over perchloroethylene was far higher than in the comparative examples above.

Net production rate after correction on accumulation was then 3280 kg/h for carbon tetrachloride and 754 kg/h for perchloroethylene.

The crude product mixture was then distilled using distillation apparatus comprising two continuously operated rectification columns. Carbon tetrachloride was obtained at a purity of 99.92%, with a content of less than 100 ppm chloroform.

As a byproduct of the reaction, hydrogen chloride was extracted at a rate of 1474 kg/h. After absorption 40 into water, 32% hydrochloric acid was extracted via line 41 at a rate of about 4606 kg/h.

Heavy ends were extracted via line 13 at a rate of around 32.6 kg/h. The contents of that stream was analysed (Table 3) and it was found to principally comprise hexachlorobenzene, hexachlorobutadiene and hexachloroethane. This equated to the production of 0.81% of those compounds, based on the weight of the net carbon tetrachloride and perchloroethylene produced in the chlorination zone. This is a significantly lower proportion of hexa-chlorinated organic impurities than were formed in the comparative examples

Example 4

The reaction unit was set up in the same way as described above in Comparative Example 1.

Fresh chlorine gas (obtained by evaporating liquid chlorine) was fed into the reactor 5 via line 1 at a rate of 2983 kg/h. Recycled chlorine was fed in to the reactor 5 via line 49 at a rate of 930 kg/h. Gaseous propylene was fed into the reactor 5 via line 2 at a rate of 200 kg/h.

Chloroform feedstock with 99.9% purity additionally comprising 50 ppm moisture and 20 ppm of amylene was fed via line 37 to the evaporator 38 and then as a gaseous diluent via line 39 at a rate of 707 kg/h into the reactor 5. A second gaseous diluent (vapourised carbon tetrachloride 99.9% and perchloroethylene 0.1%) was fed into the reactor 5 via line 36 and 39 at a rate of 1267 kg/h. Additionally, a liquid diluent (carbon tetrachloride 99.9% and perchloroethylene 0.1%) was fed into the reactor 5 via line 35 at a feed rate of 1454 kg/h. The diluent streams were added to control temperature and the molar ratio of carbon tetrachloride: perchloroethylene in the reactor 5.

A further liquid feedstock was supplied to the reactor 5 via line 3 at a feed rate of 64 kg/h. The feedstock was a byproduct stream produced in the industrial production of 1,1,1,2,3-pentachloropropane as disclosed in International patent application no. WO2016/058569. The composition in % by weight of that byproduct stream is shown below:

8.8% 1,1,3-trichloropropene
3.4% 1,1,3,3-tetrachloropropene
21.3% 1,1,1,3-tetrachloropropane
0.3% 1,1,2,3-tetrachloropropene
13.3% 1,1,1,2,3-pentachloropropane
1.1% 1,1,1,3,3-pentachloropropane
0.3% hexachloroethane
40.0% 1,1,1,2,3,3-hexachloropropane
8.4% 1,1,1,2,2,3-hexachloropropane
1.1% sum of other pentachloropropenes,
sum of oxygenated organic compounds 600 ppm and sum of phosphorous compounds which was below detection limit (1 ppm).

As can be seen, this byproduct stream comprises a range of multichlorinated propanes, propenes, many of which are isomers. These materials cannot easily be separated into individual products. Such byproduct streams are typical of waste products generated in processes for preparing chlorinated alkanes and alkenes, e.g. as disclosed in International patent application nos. WO2016/058566, WO2016/058567, WO2016/058568, WO2016/058569 and WO2017/028826.

The temperature at the reactor was 540° C. and the average content of unreacted chlorine in line 31 was 26.7% by volume.

The crude liquid product mixture was extracted from the quench column on a continuous basis at a rate of 2621 kg/h via line 15. The crude product mixture comprised 65.1% carbon tetrachloride, 34.7% perchloroethylene and 0.2% hexachloroethane. Thus the extraction rate for each compound was 1706 kg/h for carbon tetrachloride and 909 kg/h for perchloroethylene. Net production rate after correction on accumulation was then 1704 kg/h for carbon tetrachloride and 904 kg/h for perchloroethylene.

Importantly, none of the waste hydrocarbons from the byproduct feedstock were detected in the crude product stream 15, nor in the waste product stream 13.

The crude product mixture was then distilled using distillation apparatus comprising two continuously operated rectification columns. Carbon tetrachloride was obtained at a purity of 99.98%, with a content of less than 100 ppm chloroform.

As a byproduct of the reaction, hydrogen chloride was extracted at a rate of 1270 kg/h. After absorption 40 into water, 32% hydrochloric acid was extracted via line 41 at a rate of about 3969 kg/h.

Heavy ends were extracted via line 13 at a rate of around 15.2 kg/h. The contents of that stream was analysed (Table 3) and it was found to principally comprise hexachlorobenzene, hexachlorobutadiene and hexachloroethane. This equated to the production of 0.58% of those compounds, based on the weight of the net carbon tetrachloride and perchloroethylene produced in the chlorination zone. This is a significantly lower proportion of hexa-chlorinated organic impurities than were formed in the comparative examples.

Example 5

Highly pure carbon tetrachloride obtained from Example 1 and 2 above was employed in the process disclosed in WO2016/058569 to produce 3560 kg of 1,1,1,2,3-pentachloropropane having a purity of 99.9795%.

Example 6

Highly pure carbon tetrachloride obtained from Examples 3 and 4 above was employed in the process disclosed in WO2016/058569 to produce 3560 kg of 1,1,1,2,3-pentachloropropane having a purity of 99.9793%.

Example 7

Using the processes disclosed in WO2017/028826, 20 kg of 1,1,3,3-tetrachloropropene having a purity of 99.85% were produced, using highly pure carbon tetrachloride obtained as a product of the process of the present invention as a feedstock.

TABLE 1

Parameters for Preparation of Carbon Tetrachloride in the Examples

| | | Example No. | | | | |
|---|---|---|---|---|---|---|
| | | Comp. Example 1 | Comp. Example 2 | Comp. Example 3 | Comp. Example 4 | Comp. Example 5 |
| Duration | h | Current run | Design | 11 | 10.5 | 8 |
| Balance duration/period | h | — | — | 3 | 3 | 3.5 |
| Reactor temp | °C. | 585 | 585 | 540 | 540 | 560 |
| Gas diluent feed | kg/h | 4 037 | 12 019 | 3 900 | 2 000 | 1 949 |
| Liquid diluent feed | kg/h | 1211 | — | 1597 | 1518 | — |
| Fresh chlorine feed | kg/h | 3048 | 4 344 | 3 000 | 2 843 | 3 079 |
| Recycled chlorine feed | kg/h | 536 | 851 | 1 351 | 1 282 | 1 230 |
| Fresh propylene feed | kg/h | 230 | 409 | 255 | 239 | 228 |
| PER diluent feed | kg/h | — | 685 | — | 667 | 971 |
| CHM feed | kg/h | — | — | — | — | — |
| Chlorinated waste feed | kg/h | 278 | — | — | — | — |
| Outlet HCl-100% | kg/h | 1 421 | 2 156 | 1 365 | 1 258 | 1 216 |
| Outlet netto CTC | kg/h | 49 | 500 | 956 | 1 065 | 1 335 |
| Outlet netto PER | kg/h | 1 781 | 2 000 | 911 | 730 | 740 |
| Ratio CTC/PER | kg/kg | 0.03 | 0.25 | 1.05 | 1.46 | 1.80 |
| Unreacted $Cl_2$ | % vol. | 11.0 | 16.0 | 25.9 | 26.3 | 26.1 |
| Volumetric flow from the reactor | m³/h | 3 081 | 5 592 | 3 108 | 2 678 | 2 558 |
| Reactor mean residence time | s | 16.94 | 9.33 | 16.79 | 19.49 | 20.41 |
| Heating consumption | MJ/kg | 0.57 | 1.19 | 0.55 | 0.32 | 0.27 |
| Cooling consumption | MJ/kg | 2.2 | 3.71 | 2.02 | 1.27 | 0.72 |
| Hexa-chlorinated waste | kg/h | 133 | 93.1 | 18.7 | 21 | 37.6 |
| Hexa-chlorinated waste: CTC + PER | % | 7.32 | 3.72 | 1.00 | 1.17 | 1.81 |
| Hexachloro benzene (HCB) | kg/h | 71.88 | 56.66 | 10.85 | 8.64 | 22.29 |
| Hexachloro butadiene (HCBu) | kg/h | 34.37 | 23.73 | 4.19 | 6.19 | 8.56 |
| HCB: CTC + PER | % | 3.93 | 2.27 | 0.58 | 0.48 | 1.07 |
| HCBu: CTC + PER | % | 1.88 | 0.95 | 0.22 | 0.34 | 0.41 |

| | | Example No. | | | |
|---|---|---|---|---|---|
| | | Example 1 | Example 2 | Example 3 | Example 4 |
| Duration | h | 10 | 10 | 9 | 8 |
| Balance duration/period | h | 2.5 | 2.5 | 2 | 3 |
| Reactor temp | °C. | 540 | 540 | 540 | 540 |
| Gas diluent feed | kg/h | 1 998 | 1 774 | 2 210 | 1 974 |
| Liquid diluent feed | kg/h | 1107 | 1593 | 2077 | 1454 |
| Fresh chlorine feed | kg/h | 3 066 | 3 322 | 3 480 | 2 983 |
| Recycled chlorine feed | kg/h | 1 265 | 1 278 | 1 044 | 930 |
| Fresh propylene feed | kg/h | 202 | 199 | 199 | 200 |
| PER diluent feed | kg/h | — | — | — | — |
| CHM feed | kg/h | 1 023 | 1 362 | 1 867 | 707 |
| Chlorinated waste feed | kg/h | — | — | — | 64 |
| Outlet HCl-100% | kg/h | 1 308 | 1 428 | 1 474 | 1 270 |
| Outlet netto CTC | kg/h | 2 166 | 2 639 | 3 280 | 1 704 |
| Outlet netto PER | kg/h | 808 | 806 | 754 | 904 |
| Ratio CTC/PER | kg/kg | 2.68 | 3.27 | 4.35 | 1.88 |
| Unreacted $Cl_2$ | % vol. | 29.5 | 25.4 | 19.8 | 26.7 |
| Volumetric flow from the reactor | m³/h | 2 726 | 2 851 | 2 867 | 2 707 |
| Reactor mean residence time | s | 19.15 | 18.31 | 18.21 | 19.29 |
| Heating consumption | MJ/kg | 0.19 | 0.15 | 0.15 | 0.21 |
| Cooling consumption | MJ/kg | 0.70 | 0.62 | 0.67 | 0.85 |
| Hexa-chlorinated waste | kg/h | 9.2 | 23.1 | 32.6 | 15.2 |
| Hexa-chlorinated waste: CTC + PER | % | 0.31 | 0.67 | 0.81 | 0.58 |
| Hexachloro benzene (HCB) | kg/h | 4.79 | 11.87 | 13.86 | 8.26 |
| Hexachloro butadiene (HCBu) | kg/h | 2.70 | 4.86 | 11.60 | 3.98 |
| HCB: CTC + PER | % | 0.16 | 0.34 | 0.34 | 0.32 |
| HCBu: CTC + PER | % | 0.09 | 0.14 | 0.29 | 0.15 |

TABLE 2

Composition of Line 15
% wt.

| Example No. | CHM | CTC | TCE | PER | CHCE | HCBu | PCB | HCB | X |
|---|---|---|---|---|---|---|---|---|---|
| Comparative Example 1 | 0.0028 | 21.11 | 0.0129 | 78.42 | 0.25 | 0.0931 | 0.0036 | 0.0272 | 0.0815 |
| Comparative Example 2 | na | 16.83 | 0 | 78.74 | 4.22 | 0 | 0 | 0 | 0 |
| Comparative Example 3 | 0.0016 | 50.07 | 0.0028 | 48.81 | 0.94 | 0.1350 | 0 | 0.0025 | 0.0402 |
| Comparative Example 4 | 0.0013 | 41.97 | 0 | 56.83 | 0.90 | 0.2610 | 0 | 0.0110 | 0.0297 |
| Comparative Example 5 | 0.0008 | 43.67 | 0.0020 | 55.89 | 0.27 | 0.1403 | 0 | 0.0090 | 0.0160 |
| Example 1 | 0.0021 | 72.55 | 0.0044 | 27.15 | 0.14 | 0.1012 | 0.0011 | 0.0079 | 0.0441 |
| Example 2 | 0.0016 | 76.38 | 0.0043 | 23.36 | 0.13 | 0.0918 | 0.0005 | 0.0068 | 0.0196 |
| Example 3 | 0.0019 | 80.91 | 0.0030 | 18.74 | 0.27 | 0.0101 | 0 | 0 | 0.0640 |
| Example 4 | 0.0005 | 65.06 | 0.0131 | 34.74 | 0.15 | 0.0163 | 0 | 0.0036 | 0.0165 |

TABLE 3

Composition of Line 13 (Hexa-chlorinated wastes)
% wt

| Example No. | TCE | PER | CHCE | HCBu | PCB | HCB | X |
|---|---|---|---|---|---|---|---|
| Comparative Example 1 | 0.0613 | 8.4489 | 6.0881 | 25.6663 | 3.1129 | 53.6823 | 2.9403 |
| Comparative Example 2 | — | 3.7399 | 9.9153 | 25.4834 | — | 60.8615 | — |
| Comparative Example 3 | 0.0669 | 4.5332 | 9.7854 | 22.4620 | 2.1541 | 58.1281 | 2.8703 |
| Comparative Example 4 | — | 12.8946 | 13.3853 | 29.4253 | 0.7951 | 41.0727 | 2.4270 |
| Comparative Example 5 | 0.1829 | 7.9445 | 6.4213 | 22.7708 | 1.4431 | 59.2758 | 1.9616 |
| Example 1 | 0.0804 | 6.9321 | 6.0515 | 29.3514 | 2.6653 | 52.0925 | 2.8268 |
| Example 2 | 0.0882 | 18.6590 | 4.9148 | 21.0693 | 1.6495 | 51.4474 | 2.1718 |
| Example 3 | — | 7.4152 | 7.1217 | 35.6438 | 1.2262 | 42.5860 | 6.0071 |
| Example 4 | — | 7.9949 | 4.9954 | 26.0934 | 2.1931 | 54.2166 | 4.5066 |

The invention claimed is:

1. A chlorinolysis process for producing carbon tetrachloride comprising providing a chlorination zone at an operating temperature of from 400 to 600° C. with i) chlorine, ii) a $C_1$ chlorinated compound comprising 1 to 3 chlorine atoms, and iii) a carbon/second chlorine source to produce a reaction mixture, and, after a residence time, extracting a product mixture from the chlorination zone, the product mixture comprising carbon tetrachloride and optionally perchloroethylene, wherein the product mixture comprises a higher molar content of carbon tetrachloride than perchloroethylene, if present.

2. The process of claim 1, wherein the $C_1$ chlorinated compound comprising 1 to 3 chlorine atoms comprises chloroform, methylene chloride, methyl chloride, or mixtures thereof.

3. The process of claim 1, wherein the carbon/second chlorine source comprises purified optionally chlorinated alkane alkene materials having a purity level of at least about 60% by weight.

4. The process of claim 3, wherein the carbon/second chlorine source is selected from the group consisting of methane, ethane, ethene, propane, propene, dichloroethane, dichloropropane, and any combination thereof.

5. The process of claim 1, wherein the carbon/second chlorine source comprises unpurified materials.

6. The process of claim 1, wherein the carbon/second chlorine source comprises: a. phosphorous containing compounds in an amount of 5000 ppm (0.5%) or less; b. oxygen containing compounds in an amount of 5000 ppm (0.5%) or less; c. iron in an amount of 5000 ppm (0.5%) or less and/or, d. water in an amount of 1000 ppm (0.1%) or less.

7. The process of claim 1, wherein the carbon/second chlorine source comprises byproduct material from processes for preparing chlorinated alkanes, chlorinated alkenes, or both.

8. The process of claim 7, wherein the chlorinated alkanes, chlorinated alkenes, or both are selected from the group consisting of carbon tetrachloride, 1,1,1,2,3-pentachloropropane, 1,1,1,3,3-pentachloropropane, 1,1,2,2,3-pentachloropropane, 1,1,2,3-tetrachloropropene, 1,1,3-trichloropropene, 1,1,1,3-tetrachloropropane, 1,1,1,3-tetrachloropropene, 1,1,3,3-tetrachloropropene, 2,3,3,3-tetrachloropropene, and 1,3,3,3-tetrachloropropene.

9. The process of claim 7, wherein the byproduct material comprises heavy ends material, light ends material, or both.

10. The process of claim 1, wherein the carbon/second chlorine source comprises one, two, three, four, five or more optionally chlorinated alkane or chlorinated alkene compounds.

11. The process of claim 1, wherein the carbon/second chlorine source comprises carbon tetrachloride and one or more alkanes and/or alkenes and/or chlorinated alkanes and/or chlorinated alkenes having a boiling point differing from the boiling point of carbon tetrachloride by about 10° C. or less.

12. The process of claim 1, wherein the carbon/second chlorine source comprises methane, ethane, or both.

13. The process of claim 1, wherein the carbon/second chlorine source comprises chlorinated $C_{1-6}$ compounds obtained from the chlorination of $C_{1-6}$ non-chlorinated saturated and unsaturated hydrocarbons having a content of $C_1$ compounds greater than 75% mol. or 75% vol.

14. The process of claim 1, where the molar ratio of carbon tetrachloride:perchloroethylene produced in the chlorination zone is 20:1, 10:1 or 5:1 to 3:1, 2:1 or 1:1.

15. The process of claim 1, wherein the operating temperature of the chlorination zone is 400° C. to 550° C.

16. The process of claim 1, wherein the mean residence time of the reaction mixture in the chlorination zone is at least 5 seconds.

17. The process of claim 1, wherein a content of hexachlorinated organic compounds in the product mixture is 2% or less by weight of the net carbon tetrachloride and perchloroethylene produced in the chlorination zone.

18. The process of claim 1, further comprising quenching the product mixture extracted from the chlorination zone.

19. The process of claim 1, further comprising subjecting the product mixture extracted from the chlorination zone to one or more distillation steps.

20. The process of claim 19, wherein a stream rich in carbon tetrachloride is obtained from the one or more distillation steps.

21. The process of claim 20, wherein the stream rich in carbon tetrachloride has a purity level of 99.9% or higher.

22. The process of claim 1, wherein a number of carbon atoms in the carbon tetrachloride and perchloroethylene produced in the chlorination zone is more than 95% of the number of atoms in the ii) $C_1$ chlorinated compound comprising 1 to 3 chlorine atoms and iii) the carbon/second chlorine source.

23. The process of claim 1, wherein the molar ratio of HCl produced in the chlorination zone:carbon tetrachloride plus perchloroethylene produced in the chlorination zone is lower than 2.5:1, lower than 2:1, lower than 1.5:1, or lower than 1.1:1.

24. The process of claim 1, wherein the ratio by mass of carbon tetrachloride:perchloroethylene produced in the chlorination zone ranges from 1:100 to 100:0.1, or from 1:10 to 100:1, or from 1:5 to 5:1, or from 1:2 to 2:1.

25. The process of claim 1, wherein the chlorination zone is exposed to UV/visible light.

26. The process of claim 1, further comprising adding the carbon tetrachloride produced in the chlorination zone as a feedstock in a downstream process, wherein the downstream process produces a stream comprising optionally chlorinated organic compounds, and said stream is recycled hack to the chlorination zone for use as the carbon/second chlorine source.

27. The process of claim 1, wherein a crude carbon tetrachloride composition is obtained, and at least a portion of said composition is recycled hack to the chlorination zone.

28. The process of claim 1, wherein a crude carbon tetrachloride composition is produced and the produced composition is added as a feedstock in a downstream process for the production of chlorinated organic compounds, fluorinated organic compounds, or both.

* * * * *